United States Patent [19]

Shiozawa et al.

[11] 4,237,141
[45] Dec. 2, 1980

[54] DERIVATIVES OF α-METHYL-β-AMINOPROPIOPHENONE AND USE THEREOF

[75] Inventors: Akira Shiozawa, Tokyo; Shuji Kurashige, Urawa; Hiroaki Hamano, Higashimurayama; Yasuhiko Furuta, Tokyo; Masako Ikeda, Mitaka; Hiroshi Miyazaki, Kawasaki; Chiyoko Aoyagi, Urawa; Yasuo Ishii, Kashiwa, all of Japan

[73] Assignee: Nippon Kayaku Kabushiki Kaisha, Tokyo, Japan

[21] Appl. No.: 910,024

[22] Filed: May 26, 1978

[30] Foreign Application Priority Data

Jun. 2, 1977 [JP] Japan .................................. 52/63969
Jun. 2, 1977 [JP] Japan .................................. 52/63970

[51] Int. Cl.³ .................. C07D 295/10; A61K 31/445
[52] U.S. Cl. .................................. 424/267; 546/237; 260/326.5 S; 260/326.5 SF; 544/158; 544/399; 564/342
[58] Field of Search .............. 260/293.73; 424/267; 546/237

[56] References Cited

U.S. PATENT DOCUMENTS

| 3,151,124 | 9/1964 | Huebner et al. ............... 260/293.73 |
| 3,453,313 | 7/1969 | Margot et al. ...................... 424/267 |

FOREIGN PATENT DOCUMENTS

| 60306 | 11/1968 | German Democratic Rep. ..... 546/237 |
| 2362123 | 6/1974 | Fed. Rep. of Germany . |
| 35-18278 | of 1960 | Japan . |
| 39-1670 | 2/1964 | Japan . |
| 39-1671 | 2/1964 | Japan . |
| 40-20390 | 9/1965 | Japan . |
| 156622 | 2/1955 | Sweden .................................. 546/237 |
| 1213963 | 11/1970 | United Kingdom ...................... 546/237 |

OTHER PUBLICATIONS

Folia Pharmacol. Japan, vol. 58 (1962), pp. 67–77.
Chemical Abstracts, vol. 86 (1977), 11874q.
Journal of Medicinal Chemistry (1974), vol. 17, No. 8, pp. 819–824.
Journal of Medicinal Chemistry, Nov. (1969), vol. 12, pp. 994–997.

*Primary Examiner*—Norma S. Milestone
*Attorney, Agent, or Firm*—Russell & Nields

[57] ABSTRACT

Novel α-methyl-β-aminopropiophenone derivatives having bronchodilator activity represented by the following general formula:

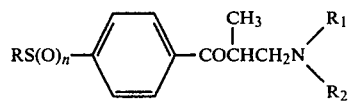

where R represents alkyl having 1–6 carbon atom benzyl or phenyl; $R_1$ and $R_2$ individually represent alkyl having 1–6 carbon atom or they form, joining to each other together with the adjacent nitrogen atom with or without intervening an atom other than carbon atom, a saturated heterocyclic ring which may be substituted with lower alkyl; n is an integer of 0, 1 or 2 on the proviso that R represents methyl or ethyl if n is 0, as well as their non-toxic salts are presented. Method of producing the new derivatives and the bronchodilatation method using them are disclosed as well.

7 Claims, 4 Drawing Figures

DERIVATIVES OF α-METHYL-β-AMINOPROPIOPHENONE AND USE THEREOF

BACKGROUND OF THE INVENTION

Most of the bronchodilators used at present for the therapy of diseases showing tracheal abnormality such as asthma are β-adrenoceptor stimulants as typically represented by isoproterenol, terbutaline, salbutamol, trimetoquinol and the like and their pharmacological action is based on that they stimulate β-adrenoceptors in tracheal smooth muscles to dilate the muscles. It is, however, well known clinically that these pharmaceutical agents also act on β-adrenoceptors present in other sites than tracheal smooth muscles and cause serious side effects such as tachycardia, vasodilatation, tremor and the like. These known bronchodilators, therefore, have a serious defect that they have to be used, upon administration, with a sufficient care for the above side effect and depending on the patient's pathological conditions. It is therefore considered at present that the essential condition for desired bronchodilators are that they selectively act only to the tracheal smooth muscles.

The inventors of the present application have made various studies for developing new pharmaceutical agents free from the foregoing defects and, as the result, discovered that the compounds represented by the above general formula (I) are very useful as new type bronchodilators in view of their mechanism of action and chemical structure, different from conventional β-adrenoceptor stimulants, in that they selectively act on the tracheal smooth muscles to thereby provide relaxation therein while causing only very weak cardiovascular effects. The present invention has been accomplished based on the above findings.

It is known that the compounds represented by the following general formula:

where R' represents n-propyl, n-butyl, cyclohexyl, phenyl, benzyl and phenetyl, R" represents lower dialkylamino, X represents oxygen or sulfur atom and A represents an organic or inorganic acid has a local anesthetic action as disclosed in Japanese Pat. No. 426,718 (Japanese Patent Publication No. 1671/1964), Folia Pharmacol Japan [vol. 58, p 67–77 (1962)] and the like.

The local anesthetic action of the compound having the following general formula:

where R', R" and A have the same meaning as above, is also disclosed in Japanese Pat. No. 426,717.

Further, Japanese Pat. No. 277,099 (Japanese Patent Publication No. 18278/1960) also describes that the compound represented by the following general formula:

where R is alkyl, $R_1$ and $R_2$ individually represent methyl or form a heterocyclic ring together with nitrogen atom, has an antibiotic effect against influenza virus.

None of these known literatures, however, contain descriptions which suggest the bronchodilatation action of the compounds according to the present invention.

SUMMARY OF THE INVENTION

The object of the present invention is, as apparent from the foregoings, to provide quite new bronchodilators capable of selectively acting on tracheal smooth muscles to dilate them while causing only very weak cardiovascular effects.

The present invention concerns new α-methyl-β-aminopropiophenone derivatives having bronchodilatation effect, their non-toxic salts, process for the production thereof, as well as human and animal bronchodilatation by using them.

The novel α-methyl-β-aminopropiophenone derivatives according to the present invention are represented by the following general formula:

where R is alkyl having 1–6 carbon atom, benzyl, or phenyl; $R_1$ and $R_2$ individually represent alkyl having 1–6 carbon atom or they form, joining to each other together with the adjacent nitrogen atom with or without intervening an atom other than carbon atoms, a saturated heterocyclic ring which may be substituted with lower alkyl; and n is an integer of 0, 1 or 2 providing that R is methyl or ethyl if n is 0, and their non-toxic salts include those of various organic and inorganic acids such as hydrochloric acid, sulfuric acid, hydrobromic acid, acetic acid, oxalic acid, citric acid, malic acid, tartaric acid, fumaric acid, maleic acid and succinic acid and the like.

The alkyl group having 1–6 carbon atom number includes, for example, methyl, ethyl, propyl, butyl, pentyl and hexyl.

The saturated heterocyclic ring includes 5- or 6-membered rings such as pyrrolidino, piperidino, morpholino, 4-methylpiperazino and the like.

The atom other than carbon atom through which $R_1$ and $R_2$ are joined includes oxygen, nitrogen, sulfur atoms and the likes.

The compounds represented by the general formula (I) can be prepared by reacting a propiophenone derivative represented by the following general formula:

where R represents alkyl having 1-6 carbon atoms, benzyl or phenyl, with formaldehyde or para-formaldehyde and a secondary amine represented by the following general formula:

where $R_1$ and $R_2$ have the same meaning as above and performing oxidation if required. Their non-toxic salts can be produced by reacting the compound represented by the general formula (I) with a physiologically non-toxic organic or inorganic acid in an adequate solvent. When para-formaldehyde is used, the above reaction is proceeded preferably in the presence of hydrochloric acid.

Bronchodilatation according to the present invention can be achieved by applying to men or animals an effective dose of the compound represented by the general formula (I) or their non-toxic salt.

The bronchodilating composition according to the present invention comprises an effective amount of the compound of the general formula (I) or their non-toxic salts and medicinal adjuvant and the composition is applied to men or animals through oral dosage or injection.

DETAILED DESCRIPTION OF THE INVENTION

In the general formula (I) of the compounds according to this invention, R is preferably alkyl having 1-4 carbon atoms or phenyl and, most preferably, methyl, ethyl, n-butyl and phenyl. Preferably, $R_1$ and $R_2$ individually represent methyl and/or ethyl or join with or without intervening an oxygen or nitrogen atom so that represents a 5- or 6-membered saturated heterocyclic ring which may be substituted with a lower alkyl having 1-6 carbon atoms, preferably, with methyl. The 5- or 6-membered saturated heterocyclic ring includes, for example, pyrrolidino, morpholino, 4-methylpiperazino or piperidino, preferably, pyrrolidino, 4-methylpiperazino or piperidino and, most preferably, piperidino.

Accordingly preferred compounds of the present invention are those of the general formula (I) where R is alkyl having 1-4 carbon atoms or phenyl; $R_1$ and $R_2$ individually represent methyl and/or ethyl or form a saturated heterocyclic ring so that represents pyrrolidino, 4-methyl piperazino or piperidino, and a more preferably, those of the formula (I) where R is alkyl having 1-4 carbon atoms or phenyl; $R_1$ and $R_2$ individually represent methyl or form a saturated heterocyclic ring so that represents piperidino and n is 0 or 2 (provided that R is methyl if $R_1$ and $R_2$ are methyl). Further preferred are the compounds where R, $R_1$ and $R_2$ are methyl and n is 0 or the compounds where R is methyl, ethyl, n-butyl or phenyl and is peperidino and n is 0 or 2. The most preferred are the compounds where R is methyl or ethyl, is piperidino and n is 0.

TABLE 1

| Compound No. | R | −N⟨R₁/R₂ | n | Salt | M.P. °C. |
|---|---|---|---|---|---|
| 1 | CH₃ | −N(CH₃)(CH₃) | 1 | fumarate | 139-141 |

TABLE 1-continued

| Compound No. | R | -N(R1)(R2) | n | Salt | M.P. °C. |
|---|---|---|---|---|---|
| 2 | CH₃ | -N(C₂H₅)(C₂H₅) | 1 | fumarate | 100-101 |
| 3 | CH₃ | -N(pyrrolidine) H | 1 | fumarate | 118-119 |
| 4 | CH₃ | -N(piperidine) H | 1 | fumarate | 127-128 |
| 5 | CH₃ | -N(morpholine) O | 1 | fumarate | 119-120 |
| 6 | CH₃ | -N(piperazine)N-CH₃ | 1 | fumarate | 150-152 |
| 7 | C₂H₅ | -N(CH₃)(CH₃) | 1 | fumarate | 143-145 |
| 8 | C₂H₅ | -N(C₂H₅)(C₂H₅) | 1 | fumarate | 145-146 |
| 9 | C₂H₅ | -N(pyrrolidine) H | 1 | fumarate | 103-105 |
| 10 | C₂H₅ | -N(piperidine) H | 1 | fumarate | 100-102 |
| 11 | C₂H₅ | -N(morpholine) O | 1 | fumarate | 108-111 |
| 12 | C₂H₅ | -N(piperazine)N-CH₃ | 1 | fumarate | 152-153 |
| 13 | CH₃ | -N(CH₃)(CH₃) | 2 | hydrochloride | 170-172 |
| 14 | CH₃ | -N(C₂H₅)(C₂H₅) | 2 | fumarate | 99-100 |
| 15 | CH₃ | -N(pyrrolidine) H | 2 | hydrochloride | 142-143 |
| 16 | CH₃ | -N(piperidine) H | 2 | hydrochloride | 144-147 |

TABLE 1-continued

| Compound No. | R | -N(R1)(R2) | n | Salt | M.P. °C. |
|---|---|---|---|---|---|
| 17 | CH₃ | -N(morpholino) | 2 | hydrochloride | 159–161 |
| 18 | CH₃ | -N(N'-methylpiperazino) | 2 | hydrochloride | 198–200 |
| 19 | C₂H₅ | -N(CH₃)₂ | 2 | hydrochloride | 158–159 |
| 20 | C₂H₅ | -N(C₂H₅)₂ | 2 | fumarate | 101–102 |
| 21 | C₂H₅ | -N(pyrrolidino, H) | 2 | hydrochloride | 149–150 |
| 22 | C₂H₅ | -N(piperidino, H) | 2 | hydrochloride | 148–149 |
| 23 | C₂H₅ | -N(morpholino) | 2 | hydrochloride | 156–157 |
| 24 | C₂H₅ | -N(N'-methylpiperazino) | 2 | hydrochloride | 217–218 |
| 25 | C₂H₅ | -N(morpholino) | 0 | hydrochloride | 160–161 |
| 26 | C₂H₅ | -N(N'-methylpiperazino) | 0 | hydrochloride | 188–189 |
| 27 | n-C₄H₉ | -N(CH₃)₂ | 1 | fumarate | 141–144 |
| 28 | n-C₄H₉ | -N(piperidino, H) | 1 | fumarate | 145–146 |
| 29 | C₂H₅ | -N(piperidino, H) | 0 | hydrochloride | 158–160 |
| 30 | C₆H₅CH₂ | -N(morpholino) | 1 | free base | 128–131 |
| 31 | C₆H₅ | -N(CH₃)₂ | 1 | fumarate | 150–152 |

TABLE 1-continued

| Compound No. | R | −N(R₁)(R₂) | n | Salt | M.P. °C. |
|---|---|---|---|---|---|
| 32 | phenyl | N-methylpiperazin-1-yl | 1 | fumarate | 161–162 |
| 33 | n-C₃H₇ | −N(CH₃)₂ | 2 | hydrochloride | 209–210 |
| 34 | n-C₃H₇ | hexahydroazepin-1-yl | 2 | fumarate | 148–149 |
| 35 | n-C₄H₉ | −N(CH₃)₂ | 2 | fumarate | 114–115 |
| 36 | n-C₄H₉ | piperidin-1-yl | 2 | hydrochloride | 143–144 |
| 37 | C₂H₅ | hexahydroazepin-1-yl | 0 | hydrochloride | 97–98 |
| 38 | benzyl | morpholin-4-yl | 2 | maleate | 143–144 |
| 39 | benzyl | piperidin-1-yl | 2 | hydrochloride | 115–116 |
| 40 | phenyl | −N(CH₃)₂ | 2 | hydrochloride | 172–174 |
| 41 | phenyl | N-methylpiperazin-1-yl | 2 | hydrochloride | 151–152 |
| 42 | phenyl | piperidin-1-yl | 2 | hydrochloride | 172–174 |
| 43 | n-C₃H₇ | −N(C₂H₅)₂ | 1 | fumarate | 118–119 |
| 44 | n-C₃H₇ | morpholin-4-yl | 1 | fumarate | 149–150 |
| 45 | benzyl | −N(CH₃)₂ | 1 | free base | 115–116 |
| 46 | n-C₄H₉ | hexahydroazepin-1-yl | 2 | hydrochloride | 179–180 |

TABLE 1-continued

| Compound No. | R | -N(R1)(R2) | n | Salt | M.P. °C. |
|---|---|---|---|---|---|
| 47 | C6H5-CH2- | -N(CH3)2 | 2 | maleate | 103-104 |
| 48 | CH3 | -N(CH3)2 | 0 | hydrochloride | 160-161 |
| 49 | CH3 | -N(C2H5)2 | 0 | fumarate | 101-102 |
| 50 | CH3 | -N(pyrrolidino) | 0 | hydrochloride | 138-139 |
| 51 | CH3 | -N(piperidino) | 0 | hydrochloride | 146-149 |
| 52 | CH3 | -N(morpholino) | 0 | hydrochloride | 159-160 |
| 53 | CH3 | -N(4-methylpiperazino) | 0 | hydrochloride | 164-165 |
| 54 | C2H5 | -N(CH3)2 | 0 | hydrochloride | 125-128 |
| 55 | C2H5 | -N(C2H5)2 | 0 | fumarate | 91-93 |

In the compounds listed in Table 1, the followings show excellent effects:
1-(4-methylthiophenyl)-3-dimethylamino-2-methylpropanone-1,
1-(4-methylsulfonylphenyl)-3-piperidino-2-methylpropanone-1,
1-(4-ethylsulfonylphenyl)-3-piperidino-2-methylpropanone-1,
1-(4-butylsulfinylphenyl)-3-piperidino-2-methylpropanone-1,
1-(4-butylsulfonylphenyl)-3-piperidino-2-methylpropanone-1,
1-(4-phenylsulfonylphenyl)-3-piperidino-2-methylpropanone-1,
1-(4-methylthiophenyl)-3-piperidino-2-methylpropanone-1 or
1-(4-ethylthiophenyl)-3-piperidino-2-methylpropanone-1 and the like.
1-(4-methylthiophenyl)-3-piperidino-2-methylpropanone-1 and
1-(4-ethylthiophenyl)-3-piperidino-2-methylpropanone-1 show particularly excellent effect.

Since the new compounds according to the present invention, theoretically, comprise two types of optical isomers because at least one asymmetric carbon atom is present in the molecule thereof, this invention includes racemates and their optical isomers to be isolated therefrom.

The reaction of the compound represented by the general formula (I) with formaldehyde or paraformaldehyde and the compound represented by the general formula (III) is preferably effected according to Mannich reaction in a conventional solvent, in particular, a lower alcohol having, preferably, 1-6 carbon atoms and, most preferably, those alcohols having 2-4 carbon atoms such as ethanol, butanol and the like.

The amine represented by the general formula (III) is usually used in the form of a salt, preferably, of hydrochloride.

Although the starting compounds have no particular restriction for their ratio, 0.2 or more, preferably, 1-4 and, more preferably, 1.5-2.0 in chemical equivalent of formaldehyde or paraformaldehyde and 0.2-5, preferably, 0.5-2 and, more preferably, 1.0-1.1 in chemical equivalent of the compound of the general formula (III) are preferably used per chemical equivalent of the compound of the general formula (II).

There is also no particular restriction for reaction temperature but the reaction can be effected at a temperature between 20°–200° C. and, preferably, 60°–160° C. Usually, the reaction is carried out under reflux of the solvent employed.

While the reaction time varies depending on the starting materials, reaction conditions employed and the like, the reaction is preferably conducted for about 3–12 hours where it is effect in a lower alcohol such as ethanol, butanol and the like under reflux of the solvent.

The desired compound can be isolated from the reaction mixture by distilling off the solvent at first, adding water to the residue thus obtained to dissolve out the contents, thereafter, neutralyzing with a base such as sodium hydroxide, potassium hydroxide, sodium hydrogen carbonate, ammonia and the like to precipitate crystals or oily products, extracting them with a non-hydrophilic organic solvent such as ether, benzene, chloroform and the like, washing the extracts with water and drying by usual method and then distilling off the solvent.

When the compound thus prepared is a thio-compound or sulfinyl compound, the compound is oxidized by an oxidizing agent, if required, into the desired compound represented by the general formula (I) of which n is 1 or 2, respectively.

The oxidation for the thio-compound or the sulfinyl compound in the present invention can be conducted in a conventional manner comprising the steps of converting the thio- or sulfinyl compound prepared into the salt of an organic or inorganic acid, wholly or partially dissolving the salt in water, methanol, ethanol, or a mixed solvent of water and methanol or water and ethanol and adding 1 or 2 equivalent hydrogen peroxide or sodium periodate at a temperature from 0° C. to room temperature thereby reacting them from several hours to overnight.

The desired compound obtained after the oxidation can be isolated from the reaction mixture by the steps of removing alcohol from the reaction mixture obtained, neutralizing the residue with a base such as sodium hydroxide, potassium hydroxide, sodium hydrogen carbonate, extracting the precipitated substance in a solvent, drying the extract with a usual drying agent and then removing the solvent by distillation.

The compound of the general formula (I) prepared by the process according to the present invention can be purified by re-crystallization of it from a suitable solvent such as cyclohexane and hexan or its non-toxic crystarizable salt from suitable solvent such as methanol, ethanol, propanol, acetone and ethyl acetate. Said salt is for example, an additional salt of an organic or inorganic acid such as hydrochloride, sulfate, hydrobromide, acetate, oxalate, citrate, malate, tartarate, fumarate, malate or succinate.

Typical compounds represented by the above general formula (II), for example, include:
1-(4-methylthiophenyl)propanone-1,
1-(4-ethylthiophenyl)propanone-1,
1-(4-n-propylthiophenyl)propanone-1,
1-(4-i-propylthiophenyl)propanone-1,
1-(4-n-butylthiophenyl)propanone-1,
1-(4-i-butylthiophenyl)propanone-1,
1-(4-phenylthiophenyl)propanone-1,
1-(4-benzylthiophenyl)propanone-1,
1-(4-methylsulfinylphenyl)propanone-1,
1-(4-ethylsulfinylphenyl)propanone-1,
1-(4-propylsulfinylphenyl)propanone-1,
1-(4-i-propylsulfinylphenyl)propanone-1,
1-(4-n-butylsulfinylphenyl)propanone-1,
1-(4-i-butylsulfinylphenyl)propanone-1,
1-(4-phenylsulfinylphenyl)propanone-1,
1-(4-benzylsulfinylphenyl)propanone-1,
1-(4-methylsulfonylphenyl)propanone-1,
1-(4-ethylsulfonylphenyl)propanone-1,
1-(4-n-propylsulfonylphenyl)propanone-1,
1-(4-i-propylsulfonylphenyl)propanone-1,
1-(4-butylsulfonylphenyl)propanone-1,
1-(4-i-butylsulfonylphenyl)propanone-1,
1-(4-phenylsulfonylphenyl)propanone-1,
1-(4-benzylsulfonylphenyl)propanone-1.

These compounds can be synthesized through condensation between the compound represented by the formula:

where R and n have the same meanings as above, and a propionyl halide utilizing Friedel-Crafts reaction. Where the compound represented by the general formula(II) is a sulfinyl or sulfonyl compound, it can be prepared by oxidizing the corresponding thio-compound with an oxidizing agent. Where the compounds of the general formula (II) are thio-compounds, most of them are known by Folia Pharmacol Japan vol. 58, p 67–77 (1962) and J. Proc. Pay. Soc., vol. 82, p 262–4 (1948), or J. Org. Chem. vol. 18, p 1209–1211 (1953). Where the compounds of the general formula (II) are sulfinyl or sulfonyl compounds, most of them are novel although they are partially known by Chemical Abstract vol. 47, 2740c. Examples of the process for the production of these sulfinyl and sulfonyl compounds are shown as follows. Synthesis of 1-(4-n-propylsulfinylphenyl)propanone-1

1-(4-n-Propylthiophenyl)propanone-1 (20.83 gr) was dissolved in 600 ml of methanol, to which was added dropwise an aqueous solution containing 22.46 g of sodium metaperiodate. The reaction mixture were stirred overnight at room temperature and, then, methanol was distilled off. The residue was extracted with chloroform and the chloroform layer was washed with water and dried over anhydrous magnesium sulfate. Usual work-up gave the crystalline product, which was recrystallized from benzene-hexane to obtain 20.8 g (yield 94.5%) of 1-(4-n-propylsulfinylphenyl)propanone-1. M.P.: 53°–56° C.

Elemental analysis ($C_{12}H_{16}O_2S$): Calculated; C: 64.25%, H: 7.19%; Found; C: 64.38%, H: 7.39%
IR (KBr) (cm$^{-1}$): 1674 (C=O), 1020 (SO).

In the same manner, the following compounds were also synthesized:

| Compound | Yield | M.P. |
|---|---|---|
| 1-(4-benzylsulfinylphenyl)propanone-1 | 59.7% | 155–156° C. |
| 1-(4-phenylsulfinylphenyl)propanone-1 | 48.4% | 98–100° C. |

Synthesis of 1-(4-methylsulfonylphenyl)propanone-1

Mixture of 108.2 g of 1-(4-methylthiophenyl)propanone-1 and 122.5 ml of 30% aqueous solution of hydrogen peroxide was heated under reflux for 15 hours. Then, the reaction mixture was poured into ice-water and the precipitated crystal was filtered, washed with water, and dried. The crystal recrystallized from ethanol to give 71.1 g (yield 56.3%) of the products. M.P. 106°–108° C.

Elemental analysis ($C_{10}H_{12}O_3S$): Calculated; C: 56.58%, H: 5.70%; Found; C: 56.71%, H: 5.73%

In the same manner, the following compounds were synthesized:

| Compound | Yield | M.P. |
|---|---|---|
| 1-(4-ethylsulfonylphenyl)propanone-1 | 81.3% | 80–82° C. |
| 1-(4-n-propylsulfonylphenyl)propanone-1 | 83.3% | 64–65° C. |
| 1-(4-n-butylsulfonylphenyl)propanone-1 | 65.3% | 63–64° C. |
| 1-(4-benzylsulfonylphenyl)propanone-1 | 68.2% | 157–158° C. |
| 1-(4-phenylsulfonylphenyl)propanone-1 | 66.1% | 104–105° C. |

The compounds represented by the general formula (III) include hydrochloride of dimethylamine, diethylamine, di-n-propylamine, di-i-propylamine, di-n-butylamine, pyrrolidine, piperidine, piperazine, morpholine, 4-methylpiperazine and the like.

The compounds represented by the general formula (I) can also be produced in the following process

[V]   [III]   [I]

where R, $R_1$, $R_2$ and n have the same meanings as foregoings, and Y represents in which X is halogen atom.

As foregoings, the compounds of the general formula (I) can be prepared by reacting propiophenones represented by the general formula (V) and secondary amines represented by the general formula (III) in the inert solvent such as ethanol, chloroform, benzene and the like at temperature between 0° and 200° C., preferably, at room temperature or, as the case may be, at the boiling point of the solvent for a time between one hour and overnight, and then by treating the reaction product in the same way as in the foregoing reaction scheme (A) if Y represents or by removing the solvent through distillation where Y represents The compounds thus prepared and represented by the general formula (I) can be purified either by recrystallization from a proper solvent or by conversion to the non-toxic salts of an organic or inorganic acid and recrystallization. The compounds represented by the general formula (V), for example, include:

The compounds represented by the general formula (V) can be prepared by condensation of the compound represented by the general formula:

(IV), where R and n have the same meanings as above, and methacryoyl halide or α-halogenomethylpropionyl halide in the presence of anhydrous aluminium chloride.

The production process according to the present invention is to be described specifically referring to examples.

EXAMPLE 1

Synthesis of 1-(4-n-propylsulfinylphenyl)-3-diethylamino-2-methylpropanone-1 (compound No. 43) and its fumarate 1-(4-n-Propylsulfinylphenyl)propanone-1 (6.73 g), diethylamine hydrochloride (6.57 gr) and paraformaldehyde (2.0 gr) were mixed with 20 ml of ethanol and 0.2 ml concentrated hydrochloric acid was added. The reaction mixture was refluxed for 24 hours. Ethanol was removed under reduced pressure. The residue was dissolved in a mixture of water and chloroform, the chloroform layer was removed and the aqueous layer was neutralized with sodium carbonate under ice-cooling. The oily product separated was extracted with ether and the ethereal layer was washed with water followed by drying over anhydrous magnesium sulfate. Ether was distilled off to give 1.43 g (yield 15.3%) of 1-(4- propylsulfinylphenyl)-3-diethylamino-2-methylpropanone-1. The oily 1-(4-n-propylsulfinylphenyl)-3-diethylamino-2-methylpropanone-1 was reacted with an equimolar amount of fumaric acid dissolved in acetone, and the solution was stirred to give crystals. The crystals were filtered and then dried. M.P. 118°–119° C.

Elemental analysis (C$_{21}$H$_{31}$NO$_6$S): Calculated; C: 59.27% H: 7.34% N: 3.29%; Found; C: 59.53% H: 7.30% N: 3.50%

In the same manner, compounds No. 27, 30, 31, 32, 44 and 45, as well as their corresponding salts listed in the Table 1 were synthesized.

EXAMPLE 2

Synthesis of 1-(4-methylsulfonylphenyl)-3-piperidino-2-methylpropanone-1 (compound No. 16) and its hydrochloride 1-(4-Methylsulfonylphenyl)propanone-1 (10.61 g), piperidine hydrochloride (6.07 g) and paraformaldehyde (2.25 g) were mixed with 15 ml ethanol and 0.2 ml of concentrated hydrochloric acid was added. The reaction mixture was refluxed for 15 hours. The reaction mixture was treated as described in the example 1, but chloroform for extraction was used instead of ether. The crystals obtained were crystallized from ether to obtain 10.23 g (yield 66.2%) of 1-(4-methylsulfonylphenyl)-3-piperidino-2-methylpropanone-1. M.P. 81.5°–82° C.

IR (KBr) (cm$^{-1}$); 1674 (C=O), 1310, 1290, 1150 (SO$_2$)

NMR (CDCl$_3$) (ppm); 1.17 (3H, d, J=7.5 Hz, CH$_3$-C), 1.38 (6H, m, CH$_2$), 2.2–3.0 (6H, m, CH$_2$-N), 3.08 (3H, s, CH$_3$S), 3.67 (1H, m, CH), 8.17 (4H, s, Mass: (M+/e) 279

Elemental Analysis (C$_{16}$H$_{23}$NO$_3$S): Calculated; C: 62.11% H: 7.49% N: 4.53%; Found; C: 61.95% H: 7.39% N: 4.45%.

The above crystal was dissolved in dry ether and gaseous hydrogen chloride was introduced thereinto to give hydrochloride. M.P. 144°–147° C.

Elemental Analysis (C$_{16}$H$_{24}$ClNO$_3$S): Calculated; C: 55.56% H: 6.69% N: 4.05%; Found; C: 55.38% H: 7.21% N: 4.23%

In the same manner, Compounds No. 13, 14, 15, 17, 18, 19, 20, 21, 22, 23, 24, 33, 34, 35, 36, 38, 39, 41, 42, 46 and 47, as well as their corresponding salts listed in the Table 1 were synthesized.

EXAMPLE 3

Synthesis of 1-(4-methylsulfinylphenyl)-piperidino-2-methylpropanone-1 (compound No. 4) and its fumarate 1-(4-Methylthiophenyl)-3-piperidino-2-methylpropanone-1 hydrochloride (13.0 g) was dissolved in 120 ml of water, and to this solution was added dropwise 7.15 ml of 30% aqueous hydrogen peroxide at 5° C. The reaction mixture was stirred at room temperature overnight and once extracted with chloroform to remove by-products. Then, the remaining aqueous layer was neutralized with sodium hydrogen carbonate and extracted again with chloroform. The chloroform layer was treated as usual work to give 9.74 g (yield 82.3%) of 1-(4-methylsulfinylphenyl)-3-piperidino-2-methylpropanone-1. M.P. 79°–81° C.

IR (KBr) (cm$^{-1}$): 1680 (C=O), 1050 (SO)

NMR (CDCl$_3$) (ppm): 1.18 (3H, d, J=7.5, CH$_3$-C), 1.40 (6H, m, CH$_2$-C), 2.78 (3H, s, CH$_3$-S), 2.2–3.0 (6H, m, CH$_2$-N), 3.70 (1H, m, CH), Mass (M+/e): 293

The above base (5.89 g) was dissolved 500 ml of acetone solution containing 3.48 g of fumaric acid. The solution was stirred at room temperature for 4 hours to give 7.27 g (yield 77.6%) of fumarate. M.P. 127°–128° C.

Elemental Analysis (C$_{20}$H$_{27}$NO$_6$S): Calculated; C: 58.66% H: 6.65% N: 3.42%; Found; C: 58.87% H: 6.72% N: 3.53%

In the same manner, the compounds No. 1, 2, 3, 5, 6, 7, 8, 9, 10, 11, 12 and 28, as well as their corresponding salts listed in the Table 1 were synthesized.

EXAMPLE 4:

Synthesis of 1-(4-methylthiophenyl)-3-piperidino-2-methylpropanone-1 (compound No. 51) and its hydrochloride 1-(4-Methylthiophenyl)propanone-1 (264.6 g), paraformaldehyde (110.4 g) and piperidine hydrochloride (196.6 g) were added to 350 ml of sec.-butanol containing 5.9 ml concentrated hydrochloride acid. The reaction mixture was refluxed for 4 hrs. Butanol was distilled off under reduced pressure, and the residue was dissolved in water. The aqueous solution was washed with ether, and was neutralized with sodium carbonate. The isolated oily product was extracted with ether. The ethereal solution was treated as usual work to give 369.3 g (yield 95.0%) of 1-(4-methylthiophenyl)-3-piperidino-2-methylpropanone-1.

IR (neat) (cm$^{-1}$): 1670 (C=O)

NMR (CDCl$_3$) (ppm): 1.15 (3H, d, J=7.3 Hz, CH$_3$-C) 1.40 (6H, m, -CH$_2$-) 2.47 (3H, s, -SCH$_3$) 2.1–3.0 (6H, m, N-CH$_2$) 3.60 (1H, m, CH)

7.90 (2H, d, J = 9.0Hz, —OC—⟨ ⟩)

The above oily product was dissolved in ether and gaseous hydrogen chloride was introduced to the solution to obtain 1-(4-methylthiophenyl)-3-piperidino-2-methylpropanone-1 hydrochloride. M.P. 146°–149° C.

Elemental Analysis ($C_{16}H_{24}ClNOS$): Calculated; C: 61.22% H: 7.71% N: 4.46%; Found; C: 61.24% H: 7.76% N: 4.36%

The reaction was conducted in the same manner as in this example, while replacing the reaction solvent from butanol to ethanol and extraction solvent for the reaction products from ether to benzene to synthesize the compounds No. 48, 49, 50, 52, 53, 55, 37, 29 and 26, as well as their corresponding salts listed in the Table 1.

EXAMPLE 5

Synthesis of 1-(4-ethylthiophenyl)-3-piperidino-2-methylpropanone-1 (compound No. 29) and its hydrochloride In the same procedures as described in Example 4 while replacing 1-(4-methylthiophenyl)propanone-1 with 1-(4-ethylthiophenyl)propanone-1, 1-(4-ethylthiophenyl)-3-piperidino-2-methylpropanone-1 was prepared.

Yield: 85.8%

Hydrochloride M.P.: 158°–160° C.

Elemental Analysis ($C_{17}H_{26}ClNOS$): Calculated; C: 62.27% H: 7.99% N: 4.27%; Found; C: 62.38% H: 8.00% N: 4.15%

EXAMPLE 6

Synthesis of 1-(4-ethylthiophenyl)-3-morpholino-2-methylpropanone-1 (compound No. 25) and its hydrochloride 1-(4-Ethylthiophenyl)propanone-1 (40.7 g), morpholine hydrochloride (25.9 g) and paraformaldehyde (9.46 g) were added to 80 ml of ethanol containing 1 ml of concentrated hydrochloric acid. The reaction mixture was refluxed for 12 hrs. After removal of ethanol, the resulting solid was recrystallized from acetone to give 58.93 g (yield 95.6%) of 1-(4-ethylthiophenyl)-3-morpholino-2-methylpropanone-1 hydrochloride. M.P. 160°–161° C.

Elemental Analysis ($C_{16}H_{24}ClNO_2S$); Calculated; C: 58.25% H: 7.33% N: 4.25%; Found; C: 58.27% H: 7.31% N: 4.17%

Compound No. 54 was also synthesized in the same manner as in this Example.

The compounds of the general formula (I) according to the present invention are used together with conventional medicinal adjuvants as a bronchodilator composition in the form of final products such as tablet, granule, dry syrup, powder, capsule, aerosol and the like. The above composition usually comprises 1.0–99%, preferably, 5–50% by weight of the compound of the general formula (I) and 1–99%, preferably, 50–95% by weight of the adjuvant.

The adjuvants used herein include the followings. For tablets, excipients an disintegrants such as lactose mannitol, calcium hydrogen phosphate and corn starch, binders such as hydroxypropylcellulose, hydroxypropylmethylcellulose and polyvinylpyrrolidone and lubricants such as magnesium stearate and calcium talc. For granules, the above composition except for the lubricant. For dry syrups, excipients such as powder sugar, mannitol, lactose and maltose, binders such as hydroxypropylcellulose, hydroxypropylmethylcellulose and polyvinylpyrrolidone and flavoring and odoring agents such as saccharin and perfumes. For powder composition, excipient and the like described with respect to the tablets and granules can be used.

Descriptions are to be made for specific examples of the compositions according to the present invention.

EXAMPLE 7

| Preparation of Tablets | |
|---|---|
| Ingredient | parts |
| Compound No. 29 | 50 |
| Lactose | 30 |
| Corn starch | 17 |
| Hydroxypropylmethylcellulose | 2 |
| Magnesium stearate | 1 |

The above composition except for magnesium stearate was added to 13 parts of isopropyl alcohol-acetone (2:8) solvent for the composition, well compounded, dried and pelletized, to which magnesium stearate was mixed. Then, they were compression-molded into tablets using a tablet machine.

EXAMPLE 8

| Compound No. 51 | 98 parts |
|---|---|
| Polyvinylpyrrolidone | 2 parts |

The above ingredients were well compounded together, further mixed with 15 parts chloroform, then pelletized using an extruding pelletizer of 0.8 mm in diameter, dried, and then shaped into granules.

The compounds of the general formula (I) according to the present invention can be applied through oral administration or injection in an effective amount, preferably, 0.1 mg/kg—3 mg/kg and, more preferably, 0.5 mg/kg—2 mg/kg at a time to thereby dilate human and animal tracheas. Accordingly, the above compounds are very useful for the therapy of diseases showing tracheal abnormality such as asthma.

Reference will now be made to pharmacological effects of the compounds according to the present invention. For the experimental evaluation of bronchodilatation and side effect of the compounds in clinical use, the guinea-pig isolated tracheal chain preparation in vitro and the canine blood-perfused tracheal preparation in situ were used for the former effect, and the canine femoral arterial preparation, the canine blood-perfused tracheal preparation and the canine isolated and cross-circulated right atrial preparation were used for the latter side effect respectively, in which the selectivity of the above compounds to trachea was expressed by the ratio between the former and the latter in comparison with that of isoproterenol which is one of the most common bronchodilators at present.

Another experiment was also conducted using mice as an index for the acute toxicity to the whole body.

PHARMACOLOGICAL EVALUATION (1) Relaxant action on the guinea-pig isolated tracheal smooth muscles and the vasodilating action on the canine anesthetized femoral arterial preparation were employed to compare the pharmacological effects of each of the compounds. The relaxant action on the tracheal smooth muscles was expressed by a molar concentration (A) of a compound required for attaining 50% relaxation in the isolated tracheal smooth muscles which had been contracted by $10^{-4}$ M histamine and the vasodilator action was expressed by an administered amount (B), μg, of the compound upon close arterial injection required for increasing the blood flow by 30 ml/min. Ratio B/A was used as an index indicative of the selectivity of each of the compounds to the tracheal smooth muscles and B/A values were calculated for each compound based on the reference B/A value for isoproterenol specified as 1. Greater B/A value shows higher selectivity to the tracheal smooth muscles. The results for the main compounds of the present invention are shown in Table 2.

(2) In order to confirm the pharmacological effect of the above compounds under the conditions closer to those in the living body, experiments were conducted for the canine blood-perfused tracheal preparation in situ and effects of decrease in the tracheal intraluminal pressure (bronchodilatation) and the effect of increase in the perfused-blood flow (vasodilator action) were compared with those of current bronchodilators in clinical use. The bronchodilator action was represented by a dose (C), μg, of a compound required for decreasing the intraluminal pressure by 20 cm $H_2O$ and the vasodilator action was represented by a dose (D), μg, of the compound required for increasing the perfused-blood flow by 5 ml/min. D/C was employed as an index indicative of the selectivity and determined based on the reference D/C value for isoproterenol specified as 1. The results are also shown in Table 2.

(3) The effect of the above compounds on the heart was studied using the canine isolated and cross-circulated right atrial preparation. The compound was administrated through arterial injection and the above effect was expressed by changes (E) in sinus rate (sinus rate/min). The results are shown in Table 2.

(4) Acute Toxicity

Approx. $LD_{50}$ value on intraperitoneal injection for mice was determined. The results are shown in Table 2.

TABLE 2

| Compound | | Pharmacological evaluation method (1) | | | Pharmacological evaluation method (2) | | | Pharmacological evaluation method (3) E | | Acute toxicity F mg/kg |
|---|---|---|---|---|---|---|---|---|---|---|
| | | A M($\times 10^{-6}$) | B (μg) | B/A | C (μg) | D (μg) | D/C $\times$ 10 | Dose (μg) | Changes of sinus rate (min) | |
| Control Compound | isoproterenol | 0.005 | 0.0053 | 1 | 0.1 | 0.01 | 1 | 0.001 | +18 | |
| | salbutamol | | | | 2 | 0.4 | 2 | | | |
| | terbutaline | | | | 0.5 | 0.2 | 4 | | | |
| | trimetoquinol | | | | 0.2 | 0.05 | 2.5 | | | |
| Compound of the invention | 4 | 300 | 800 | 3 | | | | | | 300 ~ 1,000 |
| | 10 | 200 | 700 | 4 | | | | | | 300 |
| | 16 | 60 | 750 | 12 | | | | | | 300 ~ 1,000 |
| | 22 | 60 | 580 | 9 | | | | | | 100 ~ 300 |
| | 28 | 60 | 460 | 8 | | | | | | 100 ~ 300 |
| | 36 | 20 | 360 | 18 | 333 | 100 | 3 | 100 | −2 | 100 ~ 300 |
| | 42 | 20 | 175 | 9 | | | | | | 100 ~ 300 |
| | 48 | 6 | 100 | 17 | | | | | | 100 ~ 300 |
| | 50 | 6 | 43 | 7 | | | | | | 100 ~ |
| | 51 | 6 | 240 | 40 | 62.5 | 50 | 8 | 100 | −2 | 100 ~ 300 |
| | 53 | 200 | 430 | 2 | | | | | | 100 ~ 300 |
| | 54 | 60 | 350 | 6 | | | | | | 200 |
| | 55 | 60 | 270 | 5 | | | | | | 200 |
| | 37 | 30 | 175 | 6 | | | | | | 200 |
| | 29 | 2 | 180 | 90 | 109 | 77 | 7 | 100 | −6 | 100 ~ 300 |
| | 25 | 100 | 100 | 1 | | | | | | 200 |

A: 50% effective amount for the guinea-pig isolated tracheal smooth muscles.
B: Dose required for 30 ml/min. increase in the perfused-blood flow in the canine femoral arterial preparation.
C: Dose required for 20 cm $H_2O$ decrease in the tracheal intraluminal pressure in the canine blood-perfused tracheal preparation.
D: Dose required for 5 ml/min. increase in the perfused-blood flow in the canine blood-perfused tracheal preparation.
E: Changes in sinus rate in the canine isolated and blood-perfused right atrial preparation.
F: Approx. $LD_{50}$ value (intraperitoneal injection to mice)
B/A: B/A for each compound determined based on the reference B/A value 1 for isoproterenol.
D/C: D/C for each compound determined based on the reference D/C value 1 for isoproterenol.

Based on the foregoing results, it was found that the compounds of the present invention showed higher selective effects to the tracheal smooth muscles when compared with those of conventional bronchodilators.

(5) The relaxant action of the compounds according to the present invention was also studied using the same preparations as in the Pharmacological Evaluation (1) at the presence of propranolol ($10^{-7}$ g/ml) as a β-adrenoceptor blocking agent in order to demonstrate that the bronchodilator action of the compounds of the present invention is not due to the stimulation of β-adrenoceptors.

Figure 1:
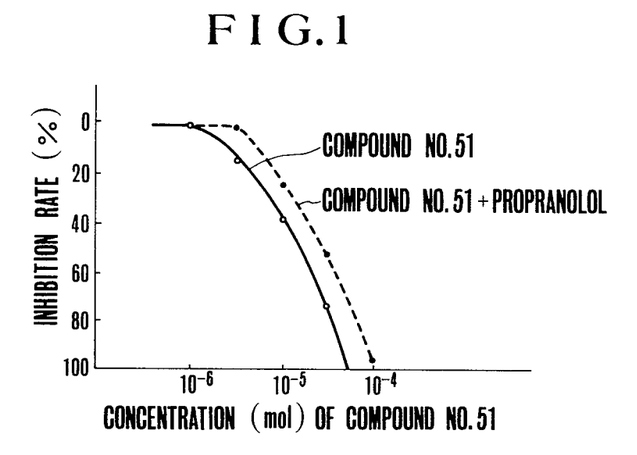
FIG. 1 is a graph showing the relation between the dose-response curve for the compound No. 51 of the present invention and that for the compound 51 in the presence of propranolol.
Figure 2:
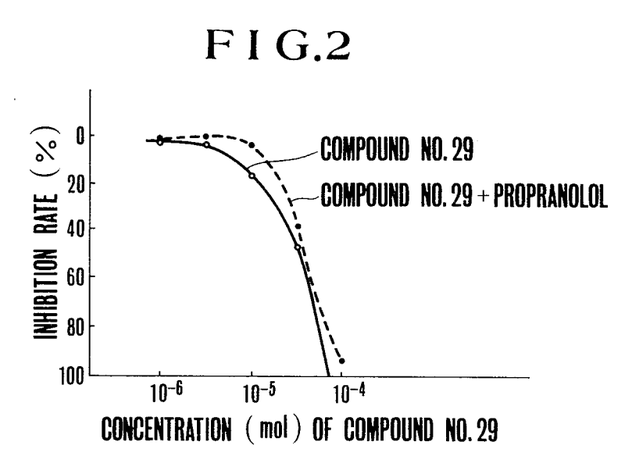
FIG. 2 shows the relation between dose-response curve for the compound No. 29 of the present invention and that for the compound 29 in the presence of propranolol.
Figure 3:
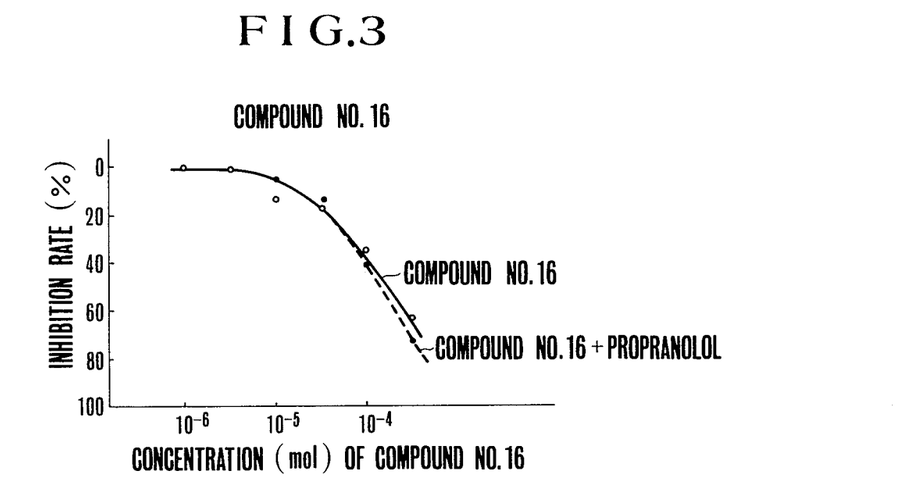
FIG. 3 shows the relation between the dose-response curve of the compound No. 16 of the present invention and that for the compound 16 in the presence of propranolol.

The results are shown in FIGS. 1, 2, 3 and 4, in which FIG. 1 shows the effect of the compound No. 51, FIG. 2 shows the effect of the compound No. 29 and FIG. 3 shows the effect of the compound No. 16 respectively. Histamine ($10^{-4}$ M in the bath medium) was applied to the guinea-pig isolated tracheal preparation to contract the muscles, and the effect of the above compounds to inhibit the contraction (%) was plotted along the ordinate on each of the points for concentration which were connected by a solid line into a curve. Then, the dose-response curve for the compound in the presence of propranolol ($2.5 \times 10^{-5}$ M) was obtained and plotted in a dotted line. In the figures, there is no substantial difference between the solid line curve and dotted line curve. This shows that the compounds of the present invention scarcely has a stimulating action on β-adrenoceptor.

Figure 4:
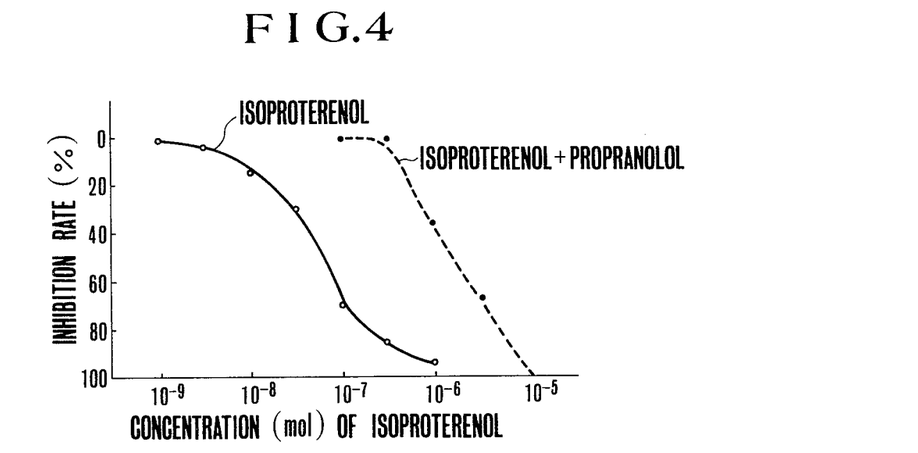
FIG. 4 shows the relation between the dose-response curve of the isoproterenol and that for the isoproterenol in the presence of propranolol.

While on the hand, in FIG. 4 showing the effect of isoproterenol which is considered to have a typical β-adrenoceptor stimulating action, there is a significant difference between the solid line where the isoproterenol is used alone and the dotted line where the isoproterenol is used together with propranolol. This shows that isoproterenol has a marked stimulating action on β-adrenoceptor.

From the foregoing experimental results, it has been found that the bronchodilator action of the compounds according to the present invention is developed, different from isoproterenol, not due to stimulating action on β-adrenoceptor but based on other mechanism of action.

What is claimed is:

1. α-methyl-β-aminopropiophenone derivatives represented by the following general formula:

wherein $RS(O)_n$-represents methylthio, ethylthio, methylsulfonyl or n-butyl-sulfonyl and represents piperidino as well as their non-toxic salts.

2. The derivatives of claim 1, wherein R S(O)n-represents methylthio or ethylthio.

3. A method of dilating human or animal tracheas by administrating an effective amount of α-methylβ-aminopropiophenone derivatives represented by the following general formula:

wherein $RS(O)_n$-represents methylthio, ethylthio, methylsulfonyl or n-butyl-sulfonyl and represents piperidino as well as their non-toxic salts.

4. The method of claim 3, wherein RS(O)n-represents methylthio or ethylthio.

5. A bronchodilator composition comprising α-methyl-β-aminopropiophenone derivatives represented by the following general formula, wherein $RS(O)_n$-represents methylthio, ethylthio, methylsulfonyl or n-butylsulfonyl and represents piperidino as well as their non-toxic salts and medical adjuvants.

6. The composition of claim 5, which comprises 1-99% by weight of the compound as the effective ingredient, and 99-1% by weight of the adjuvants.

7. The composition of claim 5, wherein RS(O)n-represents methylthio or ethylthio.

* * * * *